(12) United States Patent
Lenz et al.

(10) Patent No.: US 6,890,551 B2
(45) Date of Patent: *May 10, 2005

(54) LIGHT OCCLUSIVE PATCH

(75) Inventors: Dirk Lenz, Hamburg (DE); Robert Mayan, Buxtehude (DE); Jürgen Timm, Seevetal (DE); Sebastian Trotter, Buchholz (DE)

(73) Assignee: Beiersdorf AG, Hamburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,016

(22) Filed: Feb. 2, 1999

(65) Prior Publication Data

US 2001/0051165 A1 Dec. 13, 2001

(30) Foreign Application Priority Data

Feb. 6, 1998 (DE) .......... 198 04 665

(51) Int. Cl.⁷ .......... A61F 13/00; A61L 15/16
(52) U.S. Cl. .......... 424/443; 424/448; 424/445; 424/446; 424/447
(58) Field of Search .......... 424/443, 445, 424/449, 448

(56) References Cited

U.S. PATENT DOCUMENTS 3,908,645 A * 9/1975 Sandvig
4,538,603 A * 9/1985 Pawelchak et al.
4,709,695 A * 12/1987 Kohn et al. .......... 128/132
4,793,003 A * 12/1988 Riedel et al. .......... 2/15
4,944,040 A * 7/1990 Riedel et al. .......... 2/15
5,191,897 A * 3/1993 Meshel
5,429,592 A * 7/1995 Jensen
5,681,579 A * 10/1997 Freeman
5,844,013 A * 12/1998 Kenndoff et al.

FOREIGN PATENT DOCUMENTS

| DE | 42 33 289 | | 4/1994 | .......... C08L/75/04 |
|---|---|---|---|---|
| DE | 43 08 445 | | 9/1994 | .......... A61L/15/42 |
| DE | 195 07 120 | | 9/1995 | .......... A61F/13/00 |
| EP | 0 059 049 | | 9/1982 | .......... A61F/13/00 |
| EP | WO 89/01345 | * | 2/1989 | |
| EP | WO 89/04649 | * | 6/1989 | |
| EP | 0 335 669 | | 10/1989 | .......... A61F/13/00 |
| EP | 0 691 113 | * | 5/1995 | |
| EP | 0 691 113 | | 1/1996 | .......... A61F/13/00 |
| EP | 0 732 108 | * | 3/1996 | |
| EP | 0 732 108 | | 9/1996 | .......... A61L/15/58 |
| WO | 89/04649 | | 6/1989 | .......... A61F/13/12 |

* cited by examiner

Primary Examiner—Thurman K. Page
Assistant Examiner—Isis Ghali
(74) Attorney, Agent, or Firm—Norris McLaughlin & Marcus PA

(57) ABSTRACT

Occlusive plaster consisting of at least one layer of a foam material which is provided on the lower side with a skin-compatible self-adhesive layer.

1 Claim, 1 Drawing Sheet

1   2   3   4   5

LIGHT OCCLUSIVE PATCH

Figure 1:
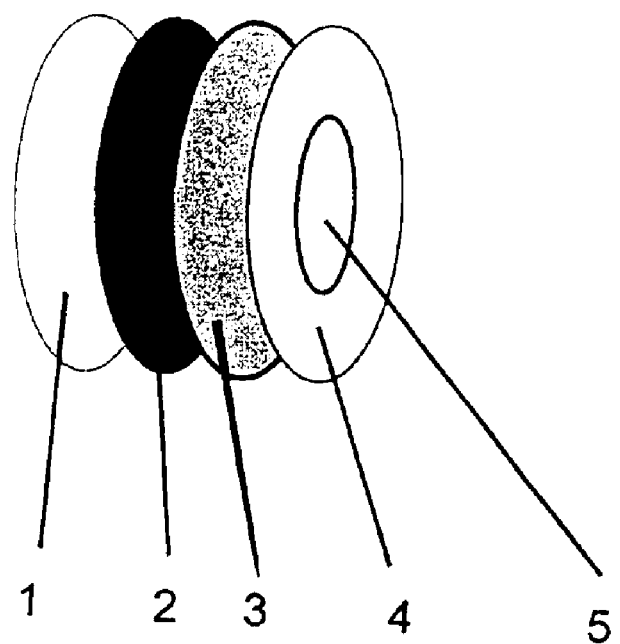

The invention relates to a self-adhesive rapid dressing which is used as an occlusive plaster.

One of the uses of occlusive plasters is to treat strabism (squint), especially in children. For this treatment the occlusive plaster is stuck in particular over the leading, working eye of the afflicted patient in order to bring about fixation of the visually weak eye.

One example of a known and commercially available occlusive plaster is the "Elastopad®" from Beiersdorf AG, Hamburg, Germany. The eye plaster consists of a transversely elastic woven viscose backing, a three-ply opaque light protection web, which is partially applied to the backing, and a zinc oxide-filled rubber composition as pressure-sensitive adhesive composition. This plaster features relatively good air permeability and water permeability but it is light-blocking (fully occlusive) only when sited over the eye with very great care. Further attributes of the plaster relate to the good fit, secure adhesion and conformability.

In addition there are further products in existence which generally employ a woven or nonwoven as the backing, which are punched out in the form of an occlusive plaster, and where there is—applied centrally—an absorbent pad which is provided with a more or less transparent liner.

However, the known plasters have a multiplicity of disadvantages.

For instance, the desired full occlusiveness is often not ensured. Owing to the relatively small and incomplete coverage of the backing with the light protection web, the lateral incidence of residual light is not ruled out, especially if the product is not sited precisely over the eye. This effect can be intensified further by the patient's movements and the associated shifting of the plaster.

Furthermore, the multi-ply structure of the occlusive plaster, composed of different materials, makes the production process complex and therefore relatively expensive.

DE 40 07 891 A1 discloses a backing material for medical purposes comprising a laminate having a first polymeric film layer, a second polymeric film layer which is produced on the first layer, and a third layer comprising a macroporous textile material which is embedded at least partially in the second layer. The first and second layers of this laminate can consist of polyurethane. The foaming of the individual layers, however, is not proposed.

The object of the invention was to provide an occlusive plaster which avoids the disadvantages of the prior art.

This object is achieved by an occlusive plaster characterized in accordance with the main claim. The subclaims relate to advantageous developments of the plaster and to a process for producing the occlusive plaster of the invention.

The invention relates accordingly to an occlusive plaster which consists of at least one layer of a foamed material and which is provided on the lower side with a skin-compatible self-adhesive layer.

To ensure occlusiveness adequately, the layer thickness of a one-layer occlusive plaster must be adequate—that is, at least 400 $\mu$m.

In one advantageous embodiment the occlusive plaster consists of a top layer made of a foamed material and an inner layer made from a foamed material, the latter layer being provided on the lower side with a skin-compatible self-adhesive layer.

It has also been found advantageous if an internal contour is printed in black on the top layer. Even with relatively low layer thicknesses of the top and/or inner layers, this contour, printed in black, ensures full occlusiveness.

In an alternative embodiment there is a black-coloured interlayer likewise formed of a foamed material between the top layer and the inner layer, over the entire area.

The foamed material employed preferably comprises PU, PP, PE or PVC foams, with particular preference being given to PU foam made of polyesterurethane.

The foamed material also preferably has a density in the dry state of from 0.03 to 0.8 $g/cm^3$, in particular from 0.1 to 0.3 $g/cm^3$.

In this case it has been found advantageous if the foam material has a layer thickness of from 0.2 to 2.0 mm, in particular from 0.3 to 0.8 mm. The smaller layer thicknesses in particular are achieved by calendering the foam material, causing it to undergo compression.

To both increase the foam density and decrease the cost of the material employed it is possible with advantage to add fillers, such as calcium carbonate, kaolin and/or alumina, to the foamed material.

To increase the mechanical stability in the lengthwise and transverse direction and to increase the tear propagation resistance of the foams, a layer of unfoamed PU can be applied to the top layer or a two-dimensional textile structure (nonwoven, knit, woven) can be embedded in the top layer.

Furthermore, an absorbent pad smaller than the adhesive area can be applied to the adhesive side of the inner layer, preferably in the middle of the backing material.

Finally, a further advantageous embodiment of the plaster is that in which the self-adhesive side is provided with at least one peelable cover sheet as a protective covering.

The inventive concept then embraces a process for producing an occlusive plaster, consisting of the following process steps.

The first step involves introducing the top layer, the inner layer and, if present, the interlayer in each case in a mixture of aqueous aliphatic dispersions of polyesterurethanes.

A foaming agent (preferably ammonium stearate, Stokal products from Stockhausen) and a dye are added to each of the mixtures.

In addition to the black-coloured interlayer, preference is given here to a skin-coloured top layer and a white inner layer.

The respective mixtures are brought to the desired degree of foaming by blowing air into them.

The coating operation begins with foam for the top layer being coated out onto a release paper and then dried.

The release paper—or, to be more precise, the particular form of the surface of the release paper—causes the dried foam and/or the top layer to take on a particularly soft, silky appearance.

Where an interlayer is provided, the foam for the interlayer is coated out onto the dried top layer and then dried.

The foam for the inner layer is coated out in the same way as for the top layer and, if appropriate, the interlayer and is likewise dried.

To produce the actual occlusive plasters, the adhesive coating is applied first of all and then the occlusive plasters are punched out.

Optional operations include the application of an absorbent pad centrally to the inner layer, and the sealed enclosure of the individual plasters.

The occlusive plaster of the invention has a host of advantages over the prior art plasters.

The full occlusiveness required of the occlusive plaster can be realized optimally, in particular, in the case of the advantageous embodiment with the black-coloured interlayer. The entire area of the plaster is light-blocking or can be made so.

Top layer, inner layer and interlayer can be produced from a single material, which is very cost-effective and minimizes the complexity.

The conformability of the plaster and the softness of the surface are unsurpassed and are ideally suited to use on the eye.

The intention of the text below is to illustrate particularly advantageous embodiments of the occlusive plaster, on the basis of a number of examples, without thereby wishing unnecessarily to restrict the invention.

In Example 1 the occlusive plaster of the invention is elucidated further at the same time by means of FIG. 1.

EXAMPLE 1

The occlusive plaster produced was composed of a total of three PU foam plies, namely a skin-coloured top layer (applied weight 77 g/m$^2$) 1, a black-coloured interlayer 2 (applied weight 33 g/m$^2$) and a white-coloured inner layer 3 (applied weight 58 g/m$^2$).

The internal black interlayer was covered effectively on both sides by the external layers so as to avoid the passage of light through the black layer.

The individual foam coats consisted of a mixture of aqueous aliphatic dispersions of polyesterurethanes (Impranil grades, Bayer AG, Leverkusen, Germany) provided with a foaming agent (ammonium stearate, Stokal products, Stockhausen, Germany) and the respective dyes (brown, black, white) and were processed by blowing air into them to give a beaten foam having a density of 0.4 g/cm$^3$.

On a coating unit with a shoe blade (coating bar) and a fan-type or radiative drier, the first beaten foam was applied to a release paper (Warren Stripkote) and knifed off at a coating-bar gap of between 0.5 and 0.7 mm. The foam was dried in a drying tunnel at a temperature increasing from 70 to 150° C. in a plurality of zones over a length of 15 m.

The application of the second layer of beaten foam with the other colour took place directly onto the first PU foam, which had been dried beforehand. Subsequently, the third layer was applied to the second layer.

The result was a fixed assembly of the three foam layers which together had a thickness of 0.8 mm and a basis weight of 170 g/m$^2$ and showed absolute opacity in the region of visible light (400 to 700 nm). Furthermore, the material was permeable to air and extremely permeable to water vapour.

Specific values are given in Table 2.

An adhesive coating 4 was applied over the entire area of the inner layer 3, an absorbent pad 5 made from a nonwoven having been applied in turn centrally to the said coating 4. The contour of the plaster was adapted correspondingly to the contour of the orbit.

EXAMPLE 2

In the same way as in Example 1 a multi-ply occlusion plaster was produced by coating with a beaten PU foam of equal density based on aliphatic polyesterurethanes (Impranil grades, Bayer AG, Leverkusen, Germany).

As a further layer on the top layer, a compact cover coat, rather than a foam (Impraperm grade, Bayer AG, Leverkusen, Germany) was applied with a basis weight of 11 g/m$^2$.

This layer is intended to increase the mechanical stability in the lengthwise and transverse direction and the tear propagation resistance of the foams.

In this embodiment the black interlayer had a basis weight of 55 g/m$^2$.

The amended embodiment showed markedly higher ultimate tensile strength in the lengthwise and transverse direction. The result was a (still) extremely good water vapour permeability but now without air permeability.

EXAMPLE 3

The chosen starting material was a single-ply blown foam based on aromatic two-component polyurethanes (High-Solids grades, from Bayer, Leverkusen, Germany) with a basis weight of 250 g/m$^2$ and a thickness of 0.4 mm.

In comparison to the beaten foams based on aqueous aliphatic polyesterurethanes in accordance with Examples 1 and 2, the material showed a markedly higher tear strength in the lengthwise and transverse direction and a markedly higher density, as well as extremely good water vapour permeability.

The tables depicted below give an overview once more of the construction of the occlusive plasters designed in accordance with the invention as in the preceding examples. The second table gives information on the physical properties of the occlusive plasters.

TABLE 1

Construction of the occlusive plasters of Examples 1 to 3

| Construction | Example 1 | Example 2 | Example 3 |
| --- | --- | --- | --- |
| Skin-coloured top coat | — | 11 g/sq.m | — |
| Skin-coloured top layer | 77 g/m$^2$ | 108 g/m$^2$ | 250 g/m$^2$ |
| Black interlayer | 33 g/m$^2$ | 55 g/m$^2$ | — |
| White inner layer | 58 g/m$^2$ | 74 g/m$^2$ | — |

TABLE 2

Physical properties of the occlusive plasters of Example 1 to 3

| Method | Example 1 | Example 2 | Example 3 |
| --- | --- | --- | --- |
| Basis weight | 170 g/m$^2$ | 250 g/m$^2$ | 250 g/m$^2$ |
| Thickness | 0.8 mm | 1.1 mm | 0.4 mm |
| Density (dried state) | 0.212 g/cm$^3$ | 0.220 g/cm$^3$ | 0.625 g/cm$^3$ |
| Ultimate tensile strength lengthwise (DIN EN ISO 527) | 6.8 N/cm | 9 N/cm | 11 N/cm |
| Elongation at ultimate tensile strength lengthwise (DIN EN ISO 527) | 400% | 410% | 400% |
| Ultimate tensile strength transverse (DIN EN ISO 527) | 6.3 N/cm | 12.5 N/cm | 11 N/cm |
| Elongation at ultimate tensile strength transverse (DIN EN ISO 527) | 470% | 540% | 400% |
| Air permeability Gurley densometer (Gurley, Troy Instruments, New York, USA) | 40 cm$^3$/(cm$^2$s) | — | — |

TABLE 2-continued

Physical properties of the occlusive plasters of Example 1 to 3

| Method | Example 1 | Example 2 | Example 3 |
|---|---|---|---|
| Water vapour permeability Method based on DAB 10*) | 5500 g/ (m² *24h) | 2900 g/ (m² *24h) | 1900 g/ (m² *24h) |

*)A material sample is fastened tightly over a sample structure (specified in accordance with DAB [German Pharmacopoeia] 10) which is filled with 15 ml of water. The sample vessel is left in a climatically controlled cabinet at 37° C. and 30% relative atmospheric humidity for 24 h and the water vapour permeability in g/(m²*24 h) is determined by back-weighing.

What is claimed is:

1. Process for producing the improved elastic light occlusive eye patch having an upper side and a lower side which is provided on the lower side with a skin compatible self-adhesive layer, consisting essentially of a top layer, an inner layer and a black colored interlayer, all layers being made of a foamed material, wherein the foamed material comprises aqueous aliphatic dispersions of polyesterurethanes, wherein the process for producing the improved elastic light occlusive eye patch comprises the following process steps:

a) preparing the top foam layer, the inner foam layer and a foamed interlayer, for each foam layer, a mixture of aqueous aliphatic dispersions of polyesterurethanes is combined with a foaming agent and a dye;

b) foaming the respective mixture to the desired degree by blowing air into it;

c) coating the foam for the top layer onto a release paper, with subsequent drying;

d) coating out the foam for the interlayer onto the dried top layer, with subsequent drying; and e) coating out the inner layer on the top layer or interlayer, with subsequent drying, to provide an assembly of foam layers having a thickness of 2 mm or less.

* * * * *